(12) United States Patent
Bultema

(10) Patent No.: US 8,855,393 B2
(45) Date of Patent: Oct. 7, 2014

(54) THREE-DIMENSIONAL X-RAY IMAGING TECHNIQUES AND DEVICES

(76) Inventor: Jonathan D. Bultema, Fargo, ND (US)

( * ) Notice: Subject to any disclaimer, the term of this patent is extended or adjusted under 35 U.S.C. 154(b) by 47 days.

(21) Appl. No.: 13/462,365

(22) Filed: May 2, 2012

(65) Prior Publication Data

US 2013/0294666 A1    Nov. 7, 2013

(51) Int. Cl.
G06K 9/00    (2006.01)

(52) U.S. Cl.
USPC ........................................... 382/131

(58) Field of Classification Search
None
See application file for complete search history.

(56) References Cited

U.S. PATENT DOCUMENTS

| | | | |
|---|---|---|---|
| 3,454,763 | A | 7/1969 | Goldenthal |
| 5,090,038 | A | 2/1992 | Asahina |
| 6,256,372 | B1 | 7/2001 | Aufrichtig et al. |
| 6,405,071 | B1 | 6/2002 | Anatoui |
| 6,876,879 | B2 | 4/2005 | Dines et al. |
| 6,904,122 | B2 | 6/2005 | Swift et al. |
| 7,369,641 | B2 | 5/2008 | Tsubaki et al. |
| 7,440,540 | B2 | 10/2008 | Kano |
| 7,715,526 | B2 | 5/2010 | Spartiotis et al. |
| 2002/0082492 | A1* | 6/2002 | Grzeszczuk .................. 600/407 |
| 2006/0170674 | A1* | 8/2006 | Tsubaki et al. ............... 345/419 |

OTHER PUBLICATIONS

"3D Accuitomo 170 Brochure", J. Morita Mfg. Corp., (Jan. 2011), 32 pgs.

"Back to Basics—Basics of Computed Tomography", (c) 2010 The American Society for Nondestructive Testing, Inc. [online]. [archived Dec. 12, 2010]. Retrieved from the Internet: <URL: http://web.archive.org/web/20101212195932/http://asnt.org/publications/materialsseval/bas>, (2010), 7 pgs.

"Sirona 3D Technology", [online]. [retrieved on May 3, 2012]. Retrieved from the Internet: <URL: http://www.sirona3d,comlgalileos3d_technology.html>, 3 pgs.

Hardy, K., "Twin Peeks—Stereo Mammography's Two Perspectives May Overcome One Mammography Limitation", [online]. Retrieved from the Internet: <URL: http://www.radiologytoday.net/archive/rt02112008p22.shtml>, (Feb. 11, 2008), 2 pgs.

* cited by examiner

Primary Examiner — Atiba O Fitzpatrick
(74) Attorney, Agent, or Firm — Schwegman Lundberg & Woessner, P.A.

(57) ABSTRACT

Embodiments of a system, device, and method used in connection with the capture, processing, and display of radiographic images for use in a three-dimensional radiographic image representation are generally described herein. In some embodiments, a digital x-ray unit is arranged to provide transmission of x-ray energy at a series of determined angles and perspectives. The transmission of x-ray energy may be captured as series of two-dimensional digital x-ray images, and provided to a processing environment. A three-dimensional radiographic image representation may be created from the series of two-dimensional digital x-ray images, and provide for display in various three-dimensional display environments. Suitable three-dimensional display environments include a stereoscopic display provided on a three-dimensional electronic display unit, and a virtual three-dimensional environment simulated with a software user interface provided on a two-dimensional electronic display unit.

20 Claims, 9 Drawing Sheets

THREE-DIMENSIONAL X-RAY IMAGING TECHNIQUES AND DEVICES

TECHNICAL FIELD

Embodiments pertain to the creation, use, and display of radiographic images. Some embodiments relate to techniques and devices configured to produce three-dimensional (3-D) radiographic representations from two-dimensional (2-D) radiographic images.

BACKGROUND

X-rays are used in a variety of industrial, scientific, and medical fields to produce radiographic images. A radiographic image may be useful to display areas of different density and composition. X-rays are used, for example, in medical applications to distinguish bone from tissue. As x-rays are passed through an object and captured by film or a digital sensor, a two-dimensional representation of all the intervening objects between the x-ray source and the sensor are provided on top of each other. Therefore, to produce a 3-D representation of some object using two-dimensional x-ray images, a 3-D reconstruction of a series of images needs to occur.

Various existing systems and techniques construct three-dimensional representations of 2-D radiographic images. For example, in the dental setting, current 3-D radiography systems are provided using computed tomography (CT) or cone-beam CT-type radiography techniques. With both techniques, an x-ray imaging system revolves around an axis relative to an area of interest, such as by rotating 360 degrees (or more) around the patient and taking 180 to 360 separate x-ray exposures per revolution. These types of systems use excessive amounts of radiation to capture a large area of interest (e.g., a patient's entire mouth), and are generally not designed to be focused on a particular area of interest. Additionally, such 3-D radiography systems are generally very expensive, and not suited for the most common procedures that occur in general dentistry practice settings. Thus, there are general needs to produce high quality three-dimensional reconstructions of radiographic images with reduced radiation exposure, and at a reduced cost and complexity.

DETAILED DESCRIPTION

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

Various techniques and device configurations for obtaining, creating, and displaying three-dimensional radiographic image representations (e.g., models, renderings, simulations, visualizations) are disclosed herein. These techniques and configurations may be used to capture two-dimensional x-ray radiographs from particular angles or perspectives useful in a three-dimensional reconstruction. These techniques and configurations further may be used to effect a three-dimensional representation of two-dimensional x-ray radiograph captures, for example, in a 3-D stereoscopic-type representation provided by a 3-D display, or in a 3-D virtual representation navigable in a software environment provided by a 2-D display. Such a 3-D virtual representation may be created from triangulation data obtained with multiple radiographic captures, digitally fused into a 3-D vector image.

For example, in some embodiments applicable to the use of x-ray imaging in a dental setting, the presently described three-dimensional x-ray capture and processing techniques may be used to turn multiple two-dimensional dental periapical-view or bitewing-view radiograph images into three-dimensional radiograph representations of these views. These representations allow visualization and measurement in all three axes—depth being the crucial added dimension. Three-dimensional representations of periapical image views, for example, may provide dental practitioners with greater diagnostic information than can currently be achieved by the comparison of two or more 2-D periapical x-rays in the practitioner's mind.

Additionally, the techniques described herein enable focused imaging of particular areas of an object or anatomy with significantly lower radiation than provided with current CT or Cone-Beam CT x-ray systems. High quality images may be produced with low radiation levels due to the fact that the x-ray energy in connection with the present techniques may be focused on an area of interest, as the energy travels directly from a positioned x-ray source through the object and hits the sensor. This provides significant benefits over CT and cone-beam CT techniques that may expose humans, animals, or objects to a higher dose of radiation as the x-rays traverse through other body structures or areas on their circular path around the area of interest. Further, a three-dimensional representation may be created from a small number of radiograph images that are each obtained with the same radiation doses as used in standard two-dimensional x-ray imaging techniques.

Figure 1:
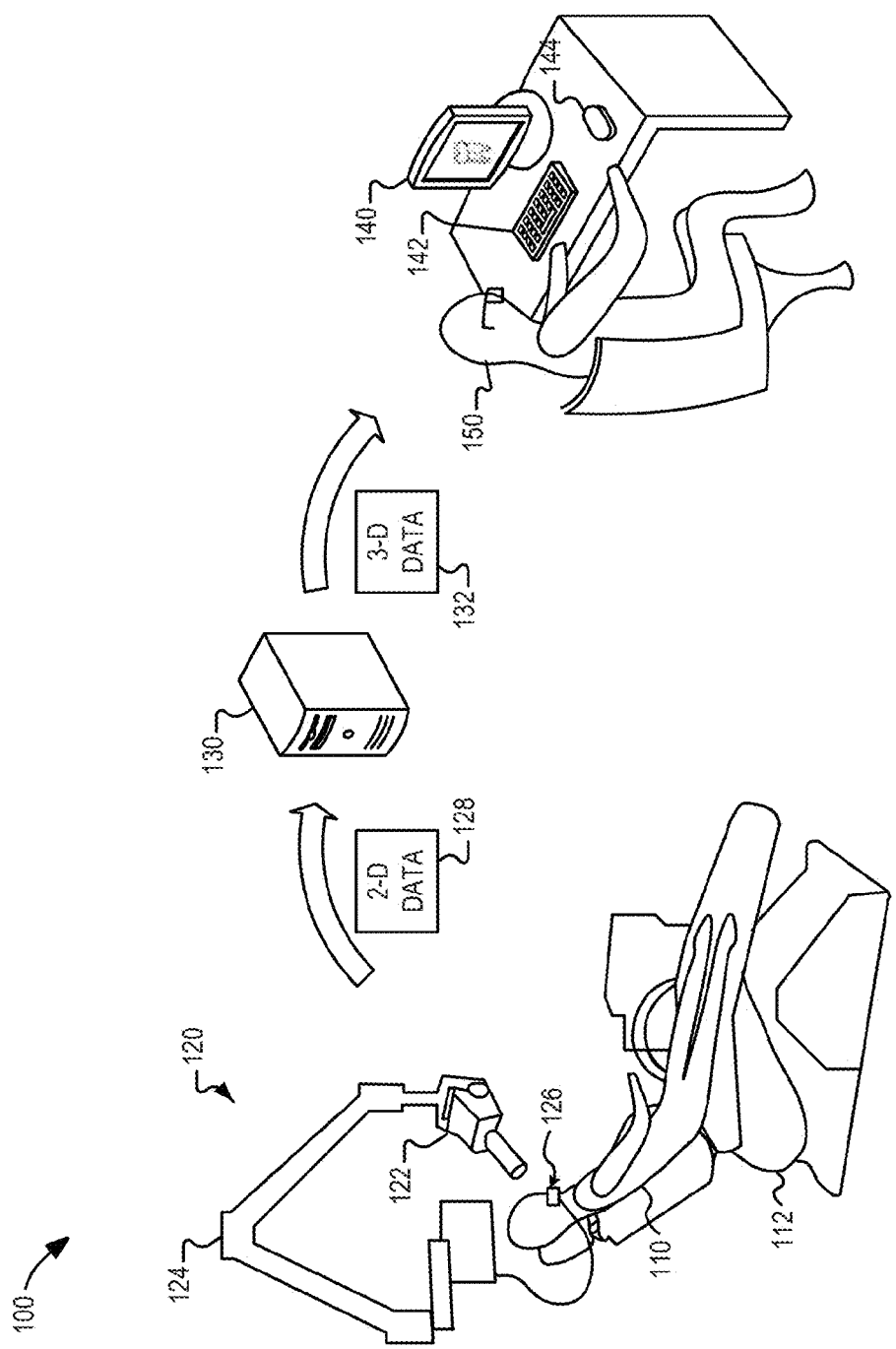
FIG. 1 is an illustration of devices and operations occurring in a radiographic image capture environment in accordance with some embodiments.

FIG. 1 provides an illustration of devices and operations occurring in a radiographic image capture environment 100, in particular an example dental environment, configured for use and operation of the presently described techniques and configurations. As illustrated, a human subject 110 (a patient) is positioned for a radiographic image capture procedure, specifically being seated in a dental chair 112. As illustrated, the radiographic image capture occurs with use of a digital x-ray unit 120 configured to aim x-ray energy towards an area of interest on the human subject 110.

The digital x-ray unit 120 includes an x-ray tube unit 122 positioned in place by an articulating arm 124 such as a permanently mounted or mobile stand. Although FIG. 1 illustrates use of the digital x-ray unit 120 from a generally fixed position, it will be understood that the digital x-ray unit 120 may also be provided through use of a handheld or portable mobile x-ray device.

The x-ray tube unit 122 may include one or more collimators within its tube structure to limit or focus radiation on a particular area, for example, to focus a beam of x-ray energy (photons) towards an area of interest. The digital x-ray unit 120 is positioned to emit the x-ray energy from the x-ray tube unit 122 towards an area of interest on the human subject 110, with the x-ray energy being transmitted through structures of the human body for capture by a digital x-ray sensor 126. For example, the digital x-ray sensor 126 may be placed intraorally and positioned for receipt of the x-ray energy passing through teeth or bones in the mouth, for capture of intraoral radiographic views such as a periapical, bitewing, or occlusal view. The digital x-ray sensor 126 may be a digital sensor such as an indirect or direct flat panel detector configured to convert x-ray photons to light or electric charge respectively, to capture the x-ray energy into a format suitable for conversion to a digital output.

Control of x-ray emissions and the x-ray imaging procedures by the digital x-ray unit 120 may occur using a combination of automatic and manual operations. For example, an x-ray operator may use a toggle switch, remote control, or other user interface to start the emission of the x-ray energy, while the digital x-ray unit 120 may be provided with automatic logic to limit or control the amount of x-ray energy emitted. Various types of manual or automatic controls and safety mechanisms may be provided in connection with the digital x-ray unit 120 to prevent unintended radiation exposure or to improve the quality of imaging procedures conducted.

The digital x-ray sensor 126 may be used to convert the x-ray energy received at the sensor from the x-ray tube unit 122 into a digital signal. The digital x-ray sensor 126 may be communicatively interfaced (via a wired or wireless connection) with the digital x-ray unit 120, a dedicated interface box (not shown), or a remote x-ray image processing system (not shown) for receipt and processing of this digital signal. For example, the digital x-ray sensor 126 may provide a serial connection such as a USB connector to a computing system executing software to capture the digital data being provided from the digital x-ray sensor 126. As another example, the digital x-ray sensor 126 may provide a wireless data transmission of a digital signal providing the digital data to a data receiver. The digital x-ray unit 120, the remote x-ray image processing system, or a like computing system may be used to convert the digital signal received or captured from the digital x-ray sensor 126 into a digital radiograph image providing binary digital x-ray image data 128.

As illustrated in FIG. 1, binary digital x-ray image data 128 obtained from the digital x-ray sensor 126 is provided to a three-dimensional x-ray image processing system 130. The three-dimensional x-ray image processing system 130 may comprise a computing system configured to interface with various hardware and software components or modules. The three-dimensional x-ray image processing system 130 may process or interface with external processes to determine two-dimensional views from binary digital x-ray image data 128 (2-D data) obtained from the digital x-ray sensor 126. The three-dimensional x-ray image processing system 130 may further combine the two-dimensional views into one or more three-dimensional views useful in a three-dimensional recreation or simulation.

As further described with the techniques herein, the three-dimensional x-ray image processing system 130 is configured to perform processing and rendering of the three-dimensional representation, in order to display the images in a correct visualization environment and display. As a result of the processing and rendering, three-dimensional x-ray representation data 132 (3-D data) is provided from the image processing system 130 to the visualization environment. The visualization environment may include an output display in connection with a stereoscopic 3-D monitor, or a virtual 3-D environment in software presented on a 2-D monitor.

Data to produce the three-dimensional representation is then transferred to the visualization environment, depicted as a virtualized 3-D software environment provided on computing system display 140 to user 150, and manipulable in connection with input devices such as a keyboard 142, a mouse 144, or like human input devices or human input recognition components. The user 150 (e.g., a dentist, doctor, radiologist, or other suitable user) may interact with the computing system display 140 or the computing system coupled to the display (not shown) to change the horizontal or vertical adjustment, views, perspective, resolution, and like parameters of the 3-D representation for example. Alternatively, the visualization environment may be provided in connection with a 3-D stereoscopic computer display (not shown), which may or may not require the use of 3-D stereoscopic glasses from the user.

The 3-D representation provided on display 140 may also be provided in connection with any number of radiology imaging systems, software applications, or techniques relevant to the display of radiographic images. For example, the 3-D representation may integrate with a radiology imaging application that allows the user (such as a doctor, dentist, or radiologist) to take notes, make markings, measurements, and perform other interactions with the 3-D representation or specific images from the 3-D representation.

Figure 2:
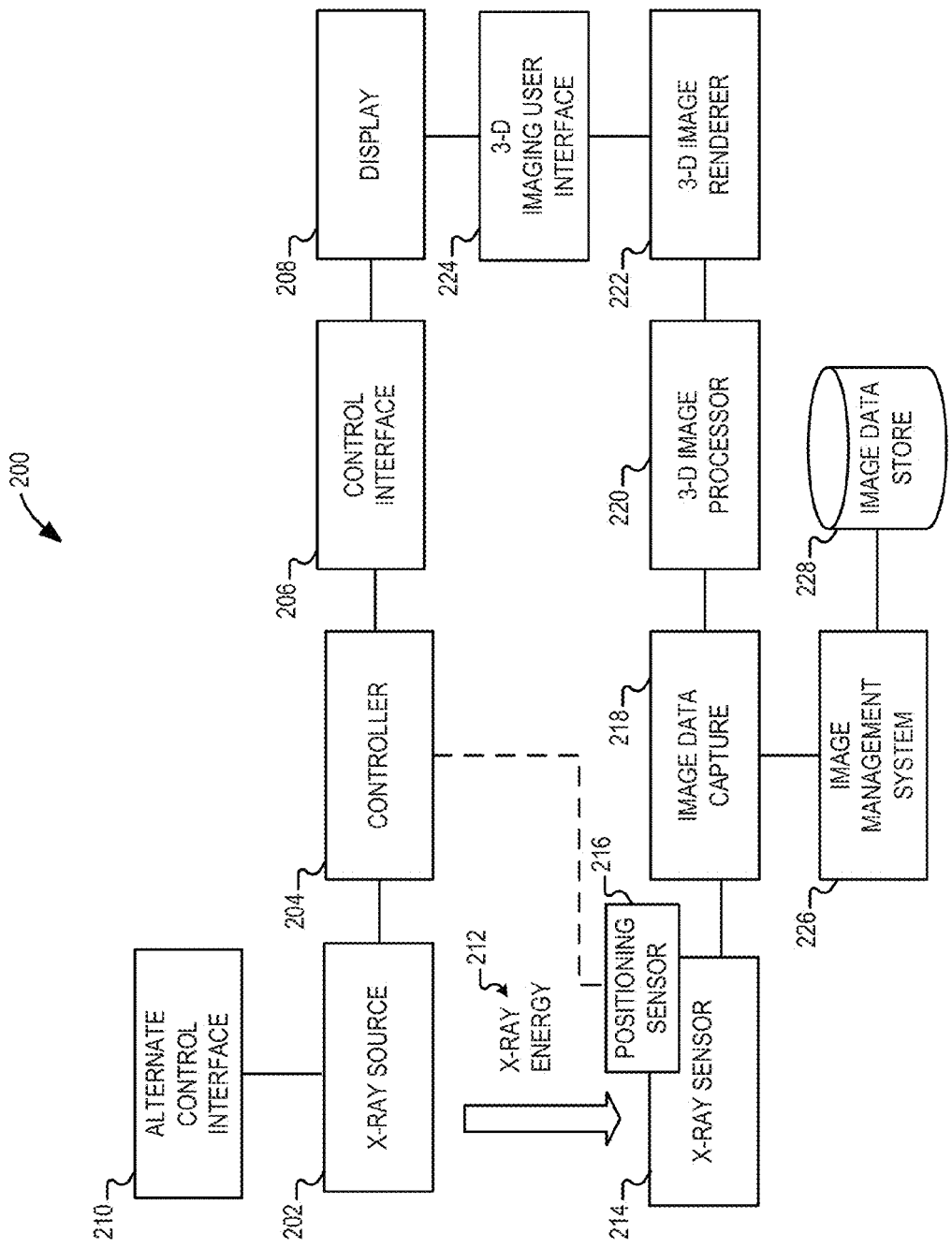
FIG. 2 is a block diagram of a configuration of three-dimensional radiographic imaging capture and processing components in accordance with some embodiments.

FIG. 2 illustrates a block diagram of a configuration of three-dimensional radiographic imaging capture and processing components 200 arranged in accordance with some embodiments. As shown, multiple components are illustrated for the capture and processing of two-dimensional x-ray images into three-dimensional x-ray representations. It will be understood that many of such multiple components may be integrated together in a single system or device configuration as appropriate, and such components may not be separated from each other.

As illustrated, an x-ray source 202 is operably coupled to a controller 204. The x-ray source 202, for example, may be a digital x-ray unit having an x-ray tube configured to generate and emit x-ray energy 212 and a collimator configured to filter or focus the x-ray energy 212 from the x-ray tube towards an output. The controller 204 may be used to control the generation and emission of the x-ray energy 212 from the x-ray source 202. For example, the controller 204 may provide logic used to provide a specific amount of x-ray energy, or timing of one or more transmissions of the x-ray energy 212.

The controller 204 is operably coupled to a control interface 206 configured for providing user control of the controller 204 and the x-ray source 202. For example, the control interface 206 may be provided in the form of a switch, button, or other hardware control operable by a human to toggle the emission of the x-ray energy 212 from the x-ray source 202. Alternatively, the control interface 206 may be provided in connection with a software user interface (not shown) operably coupled to a hardware device configured to transmit digital commands to the controller 204. In some embodiments, the control interface 206 may be further coupled to a display 208 which may provide the software user interface to one or more users to control an interface which results in the transmission of digital commands to the controller 204. The display 208 may also be used to provide the status of operations or procedures with the controller 204 or the x-ray source 202.

In addition, the x-ray source may also be provided with an alternate control interface 210. For example, this may include a switch, button, or other hardware control operable by a human to abort the emission of the x-ray energy 212 from the x-ray source 202. Moreover, multiple control interfaces including a combination of manual and automated control interfaces may be used to control the x-ray source 202.

The x-ray energy 212 is emitted from the x-ray source 202 through an object of interest, for example a physical area of interest or object to be examined with x-rays, for capture by an x-ray sensor 214. The x-ray sensor 214 may be a digital sensor adapted for external or internal placement to the human, animal, or object of interest, and may take any of the number of forms described herein.

In some embodiments, the controller 204 used for the x-ray source 202 is operably coupled to either or both of the x-ray sensor 214 or a positioning sensor 216. For example, the controller 204 may obtain information from the x-ray sensor 214 to ensure that the x-ray sensor 214 is positioned correctly or is capturing x-ray energy 212 successfully. The x-ray sensor 214 may include or may be operably coupled to the positioning sensor 216 to provide data used in connection with the location of the x-ray source 202. This may include positioning data provided to the controller 204 to enable the x-ray source 202 to adjust one or more components to target the x-ray energy 212 towards a particular area of interest, or adjust one or more transmissions of the x-ray energy 212 to converge at a particular angle of interest.

Digital data or signals produced from the x-ray sensor 214 may be provided to an image data capture component 218. The image data capture component 218 may operate to convert the digital signals into a binary representation of an x-ray image using any number of compressed or uncompressed digital imaging formats, including but not limited to Tagged Image File (TIF), Bitmap-Windows Pattern (BMP), Joint Photographic Experts Group (JPEG), JPEG Lossless, JPEG 2000, and Digital Imaging and Communications in Medicine (DICOM) (including the various pixel data image standards implementable in a DICOM-format data object).

The one or more radiographic images produced from the image data capture component 218 may in some embodiments be provided to an image management system 226. The image management system 226 may be coupled to an image data store 228 used to provide storage or archiving of the radiographic images, or of three-dimensional representations produced from the radiographic images. The image management system 226 and the image data store 228 may in some embodiments be provided by a picture archiving and communication system (PACS) or similar digital system for storage and access of the radiographic data. The image management system 226 and the image data store 228 may be further integrated or communicatively coupled with other information systems such as a digital medical records system, radiology information system (RIS), a subspecialty (e.g., dental) PACS, a cloud computing image storage system, or hospital information system (HIS).

The two-dimensional radiographic images obtained from the image data capture component 218 may be provided to a 3-D image processor component 220. In some embodiments, a three-dimensional x-ray image processing system such as image processing system 130 of FIG. 1 may provide both of the 3-D image processor component 220 and the 3-D image renderer component 222.

The 3-D image processor component 220 may be configured to receive or collect sets of 2-D radiographic images from the image data capture component 218, and provide a three-dimensional reconstruction of a series of two-dimensional images from previously captured data. For example, the 3-D image processor component 220 may locate and select a series of images captured about a certain view or perspective of a certain object, and perform 3-D image construction techniques to combine, interpolate, collate, and otherwise integrate the images together in a 3-D representation.

The 3-D image renderer component 222 may be used to provide additional image rendering data relevant to the display of graphics in a 3-D simulation environment. In some embodiments, the 3-D image renderer component 222 may be used to provide definition to a three-dimensional virtual model, for example to generate a series of voxels (volumetric pixels) having particular shading, coloring, and graphical characteristics to represent the image data in a virtual three-dimensional space. The output of the 3-D image renderer component 222 may be provided as a vector image format, such as a STL, VRML, DXF, 3DS, PLY, OBJ, U3D, DXF, or other 3-D vector format.

The 3-D imaging user interface 224 may be used to display a visual representation of the three-dimensional radiographic representation provided from the 3-D image processor component 220 and the 3-D image renderer component 222 to a human user. In some embodiments, the imaging user interface 224 may provide a virtual software environment allowing user interaction with a representation provided in a modeling environment, with movement of a displayed object available among multiple axes in three virtual dimensions. In this embodiment having a virtual software environment, output of the three-dimensional radiographic representation may be provided on the display 208, where the display 208 may be provided from a two-dimensional display such as a liquid crystal display (LCD) or light emitting diode (LED) screen.

In another embodiment, the imaging user interface 224 may be provided in connection with a set of digitally displayed stereoscopic images used to create a perception of three-dimensional depth by a viewer of the three-dimensional radiographic representation. For example, a set of stereoscopic images that are polarized according to certain colors may be output on the display 208. Output of the three-dimensional radiographic representation on the display 208 may also occur in connection with a 3-D video display such as a 3-D monitor, 3-D television, or like 3-D viewing equipment. Such a 3-D video display may be viewed by a human user with active or passive 3-D viewer glasses suited to the polarity of the stereoscopic images. Other three-dimensional display techniques such as "glasses-free" 3-D displays using autostereoscopy may also be used to provide the display 208.

Moreover, separate displays for display 208 may be provided in connection with the display used for the control interface 206 and the display used for the 3-D imaging user interface 224. Variations may be made to the imaging capture and processing components 200 to adapt to the particular processing or visualization environment.

Figure 3:
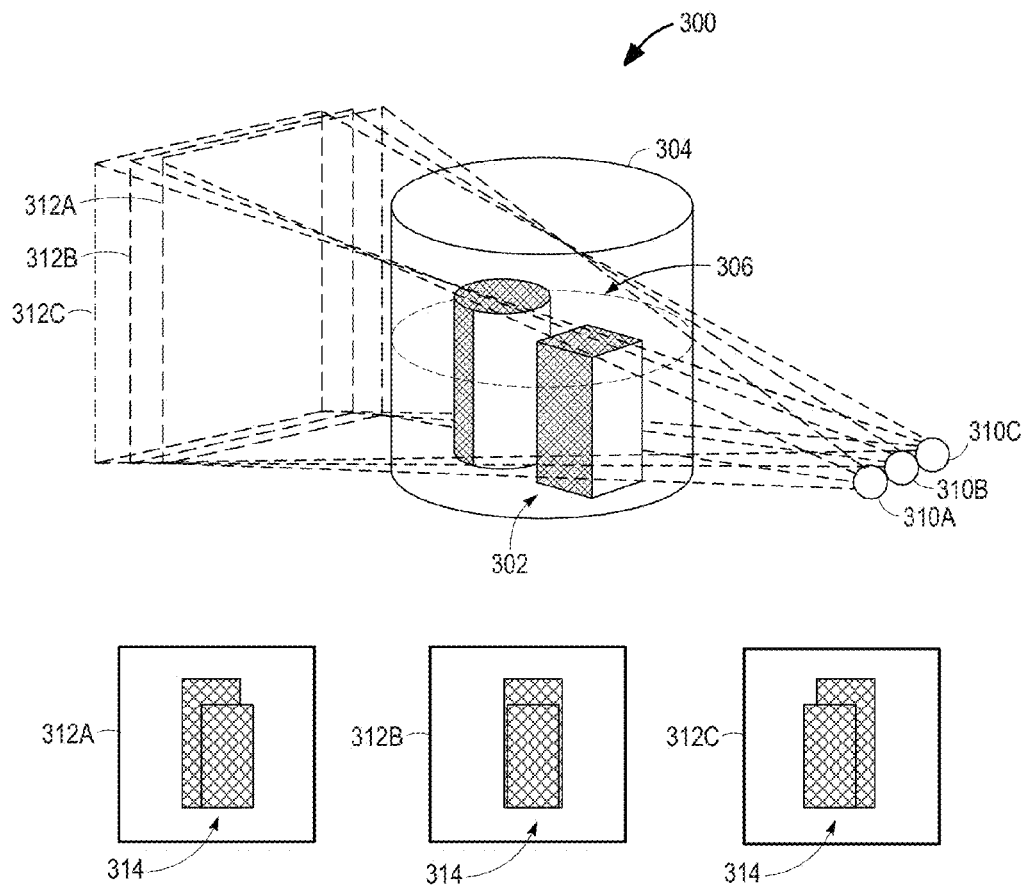
FIG. 3 is an illustration of triangulated x-ray image capture for use in a three-dimensional radiographic representation in accordance with some embodiments.
Figure 4:
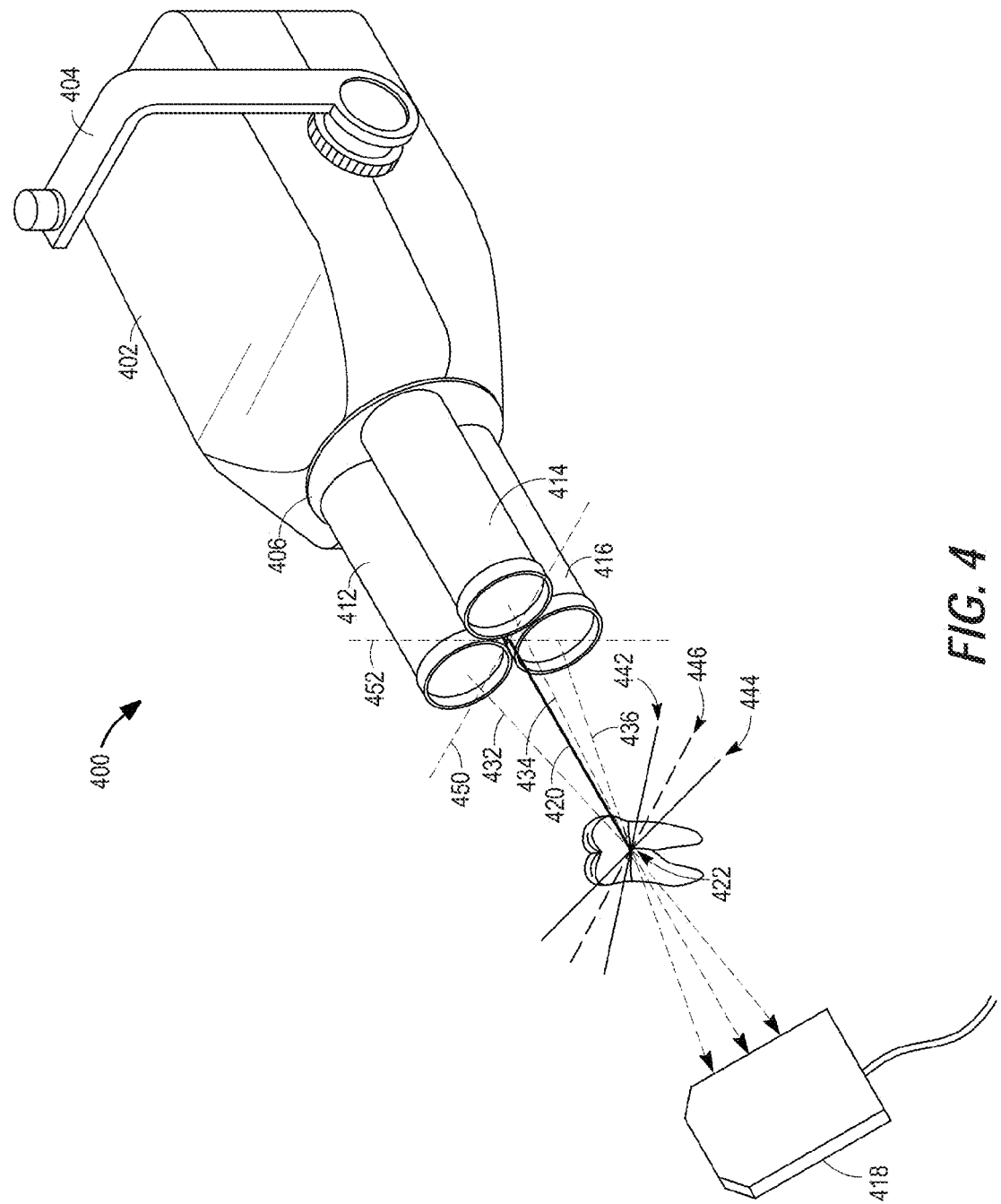
FIG. 4 is an illustration of a use scenario of an x-ray unit having multiple x-ray tube heads configured for producing x-ray images for use in a three-dimensional radiographic representation in accordance with some embodiments.
Figure 5:
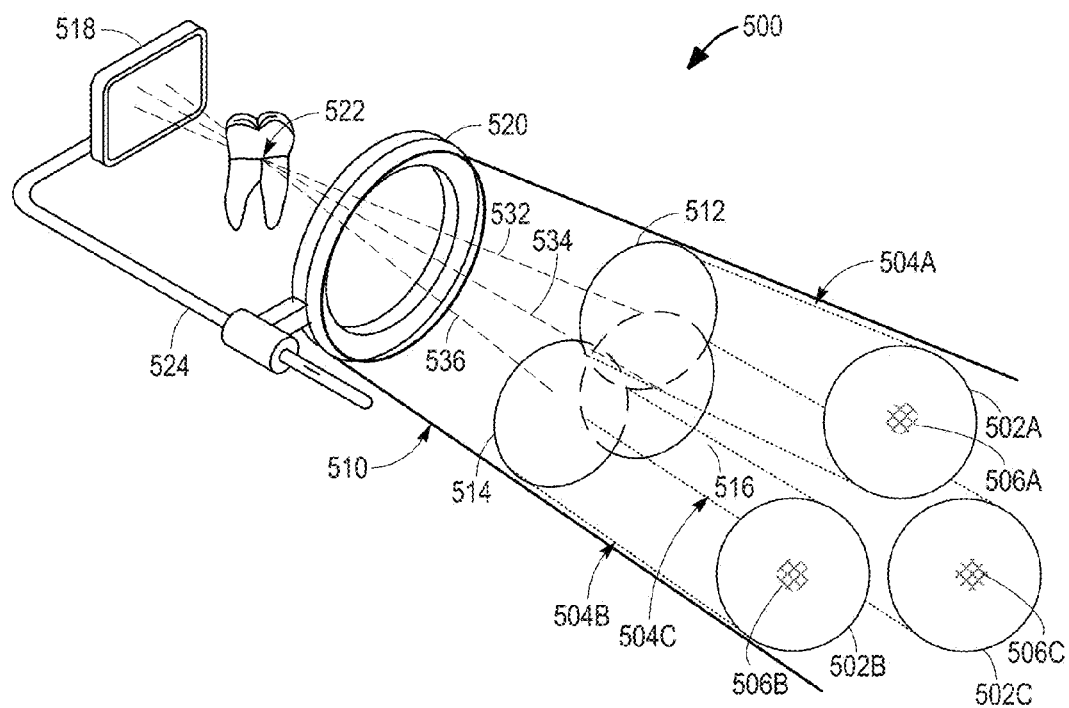
FIG. 5 is an illustration of a use scenario of a x-ray unit having a single x-ray tube head with multiple internal collimators configured for producing x-ray images for use in a three-dimensional radiographic representation in accordance with some embodiments.
Figure 6A:
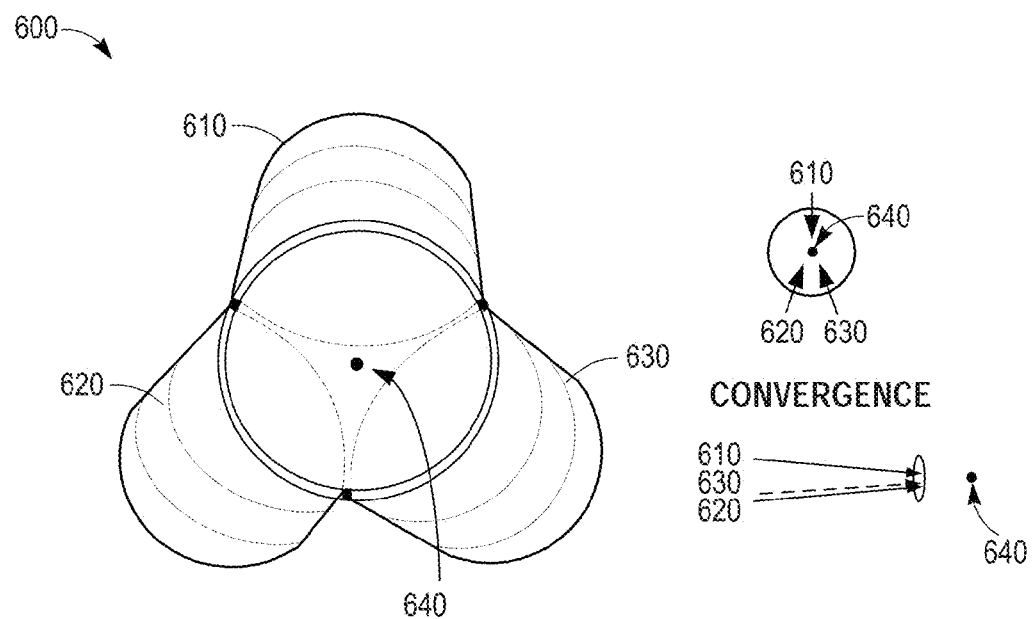
FIG. 6A is an illustration of a series of round-shaped x-ray tubes configured for converging towards a center axis in accordance with some embodiments.
Figure 6B:
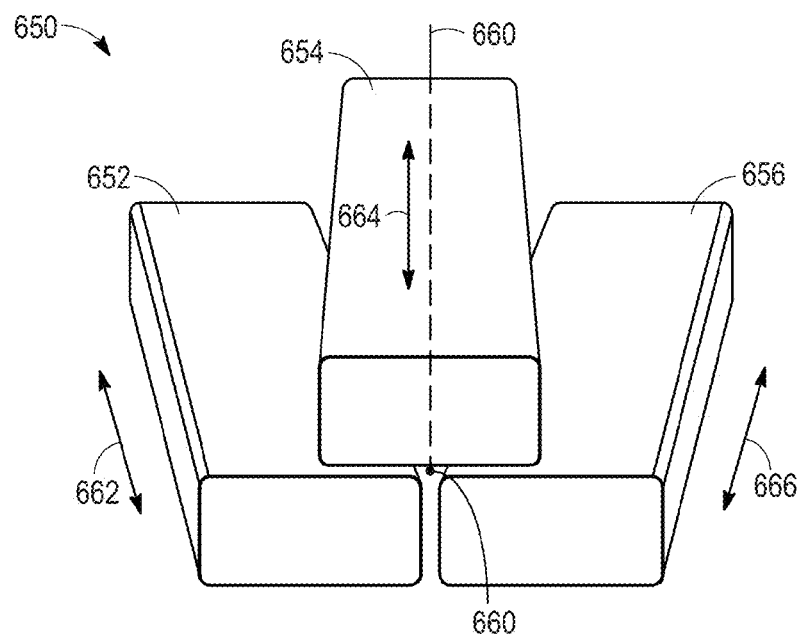
FIG. 6B is an illustration of a series of rectangular-shaped x-ray tube heads configured for converging towards a center axis used in accordance with some embodiments.

According to the presently described embodiments, a series of radiographic images may be captured for reconstruction in a 3-D radiographic representation. FIG. 3 provides an illustration of triangulated x-ray image capture using a plurality of x-ray sources. FIGS. 4 and 5 provide illustration of x-ray device configurations used to obtain and capture 2-D radiographic images from particular positions (e.g., at determined angles, from determined distances, using determined spacing) for use in creation of a 3-D radiographic representation. FIGS. 6A and 6B provide illustration of x-ray tube configurations used to manipulate and adjust the specific positions of the x-ray source for capture of the 2-D radiographic images in a triangulated x-ray device configuration. Further, FIG. 6A illustrates a triangulated round tube configuration such as could be used with internal collimation techniques, while FIG. 6B illustrates a triangulated rectangular tube configuration such as could be used with rectangular collimation techniques. These configurations are provided as illustrative examples, as other device and x-ray source configurations consistent with the techniques described herein may be used to obtain images for use in a three-dimensional radiographic representation.

In some embodiments, an x-ray system may be arranged to obtain a series of x-ray images at fixed converging angles. For example, the x-ray sources may be spaced at a fixed number of degrees apart, such a degree selected between a range of 5-25 degrees, relative to a convergence point where the x-ray transmissions converge (or would converge). Use of fixed converging angles to arrange the position of multiple sources of the x-ray energy enables a scenario in which neither the object being x-rayed, the radiographic sensor, nor the x-ray unit needs to move or rotate to produce a series of images for use in a 3-D radiographic representation. Providing radiographic image capture with such an arrangement may be performed in connection with a standard direct-beam x-ray positioning, and may not require the use of panoramic, fan slice, or rotational slice x-ray techniques to obtain images for use in a 3-D radiographic representation.

An x-ray unit may be configured to provide the emission of x-ray energy at the fixed converging angles from multiple sources. This may be provided from an x-ray unit configuration providing two x-ray sources (e.g., two x-ray tube heads), a configuration providing three x-ray sources (e.g., three x-ray tube heads), or like configurations providing for any number of multiple x-ray sources. As explained below, the multiple x-ray sources may be arranged to transmit x-ray energy at defined angles to obtain images useable in a 3-D reconstruction. Other configurations using four or more x-ray sources arranged at defined angles or configurations may also be possible using such techniques.

FIG. 3 provides an illustration of a horizontally-aligned, multiple-source x-ray image capture scenario 300, occurring from a plurality of x-ray sources 310A, 310B, 310C aligned along a single axis. Each of the x-ray sources 310A, 310B, 310C transmits x-ray energy towards a path that intersects an area of interest 302. As the x-ray energy travels from the x-ray sources 310A, 310B, 310C to a sensor (not shown), radiographs 312A, 312B, 312C of the area of interest 302 are produced. As shown, each of radiographic images (radiographs) 312A, 312B, 312C provide a capture of objects 314 in the area of interest 302, from varying perspectives and angles.

The three-dimensional image reconstruction techniques disclosed herein may be used to reassemble the radiographic images 312A, 312B, 312C to generate a three-dimensional perspective of radiographs of the area of interest 302, based on a combination of imaged objects 314 of the area of interest 302. In contrast, other volumetric imaging techniques such as a CT scan are designed to capture a "slice" of the circular volume 304 around the area of interest 302 (for example, with slice 306). Each CT imaging volume includes a large number of image slices, and such "slices" are in turn produced from a large number of x-ray exposures rotating around the area of circular volume 304. Therefore, the 3-D image produced from the presently described triangulated x-ray imaging techniques may be produced with far fewer radiograph image captures (and radiation exposure) than with CT-type techniques.

As illustrated in FIG. 3, a series of radiographic images, such as two, three, or more images, may be captured from each of a series of varying specific angles to obtain an appropriate perspective needed to create and construct a three-dimensional representation. For example, the angles of multiple collimating x-ray tube heads attached to one x-ray unit housing could be arranged to be spaced approximately between the range of 5-25 degrees between x-ray heads, relative to an axis intersecting a convergence point of the x-ray energy, to obtain x-ray images offset relative to each other at a determined angle. Likewise, an x-ray unit embodying a single x-ray tube head with multiple internal collimating x-ray sources arranged at converging angles may be used to transmit triangulated x-ray energy towards an area of interest.

FIG. 4 provides an illustration of a use scenario 400 of an x-ray unit 402 providing three x-ray tube heads 412, 414, 416 provided in connection with triangulated x-ray imaging techniques in accordance with some embodiments. Using the techniques described herein, a single two-dimensional x-ray image captured from use of each of the x-ray tube heads 412, 414, 416 may be provided for use in a three-dimensional radiographic representation.

As illustrated, x-ray unit 402 is coupled to a mounting bracket 404 and may be positioned (e.g., swiveled, pulled away or closer, or otherwise moved) relative to a location of interest, such as a human, animal, or object to be examined with x-rays. The three x-ray tube heads 412, 414, 416 are positioned at an angle with respect to an intersecting axis 420. The intersecting axis 420 intersects a convergence point 422 of the x-ray energy as the x-ray energy is transmitted from the x-ray tube heads 412, 414, 416 at a particular distance from the area of interest. For example, the convergence point 422 may be located approximately six inches away from the x-ray source in a separate tube head system from the edge of the x-ray tube heads 412, 414, 416. This positioning enables the transmission of x-ray energy in paths along x-ray energy axes 432, 434, 436 from x-ray tube heads 412, 414, 416 respectively, reaching x-ray sensor 418. The x-ray energy transmitted along axes 432, 434, 436 converges at the convergence point 422 within or near the area of interest to be x-rayed, and then disperses as it continues towards the x-ray sensor 418.

Using the arrangement of FIG. 4, the x-ray unit 402 may be configured to maintain a "fixed" angle between three x-ray tube heads 412, 414, 416 using two horizontally and one vertically positioned x-ray tube heads, such as horizontally-oriented x-ray tube heads 412, 414 located about a first axis 450 and a vertically-oriented x-ray tube head 416 located about a second axis 452 that intersects the first axis 450 at a substantially parallel angle. All three x-ray tube heads 412, 414, 416 are positioned to provide an equal convergence toward a center point. Thus, the horizontally-oriented x-ray tube heads 412, 414 may also have a slight vertical orientation as well. In other embodiments, multiple x-ray tube heads may be positioned along a same horizontal or vertical axis, positioned to provide an equal convergence toward a center point.

As illustrated, the x-ray tube head 416 may be mounted on the x-ray unit 402 to position the x-ray tube head 416 "below" the x-ray tube heads 412, 414. In an alternative configuration, the x-ray tube head 416 may be mounted on the x-ray unit 402 to position the x-ray tube head 416 "above" the x-ray tube heads 412, 414. In some embodiments, rotation of the multiple x-ray tube heads 412, 414, 416 relative to the x-ray unit 402 may be provided by rotating plate 406 to re-position the x-ray sources. Such a configuration may enable an enhanced "triangulation" effect to provide a 3-D representation using images from a rotated group of x-ray tube heads. In the viewing of such a 3-D representation, the representation may be viewed or rotated not just from horizontal left and right perspectives (or along a single axis), but from vertical up and down perspectives (along a second axis) as well. This is in addition to a depth perspective (a third axis) that is obtained through the use of triangulated x-ray capture from multiple x-ray sources.

When the x-ray unit 402 is positioned at the determined distance from the convergence point 422, a first x-ray energy axis 432 that corresponds to the path of the x-ray energy emitted from the x-ray tube head 412 will converge, at the convergence point 422, with the second x-ray energy axis 434 that corresponds to the path of the x-ray energy emitted from the second x-ray tube head 414, and the third x-ray energy axis 436 that corresponds to the path of the x-ray energy emitted from the third x-ray tube head 416. In accordance with the techniques and configurations described herein, the three x-ray tube heads 412, 414, 416 may be positioned to emit x-ray energy, for example in the range of approximately 5-25 degrees from each other relative to the convergence point 422.

As illustrated and previously described, the three x-ray tube heads 412, 414, 416 emit x-ray energy in paths along the first x-ray energy axis 432, the second x-ray energy axis 434, and the third x-ray energy axis 436 respectively. The x-ray energy from each source continues until received at the digital x-ray sensor 418. The path for the x-ray energy from the first x-ray tube head 412 and the second x-ray tube head 414 is provided perpendicular to a plane 442 at the area of interest, to obtain an x-ray image of all objects perpendicular to the plane 442 and located between the first x-ray tube head 412 and the x-ray sensor 418. The path for x-ray energy from the second x-ray tube head 414 is provided perpendicular to a plane 444 (angled slightly from plane 442) at the area of interest, to obtain a second x-ray image of all objects perpendicular to the plane 444. The path for x-ray energy from the third x-ray tube head 416 is provided perpendicular to a plane 446 (angled slightly from planes 442, 444) at the area of interest, to obtain a third x-ray image of all objects perpendicular to the plane 446. Thus, the x-ray energy will be provided towards an area of interest surrounding the convergence point 422 (e.g., in a dental setting, a specific tooth, set of teeth, or dental structure) at series of varying angles based on the angle of x-ray energy axes 432, 434, 436.

The images produced from the x-ray sensor 418 from the x-ray energy provided from each of the first, second, and third x-ray tube heads 412, 414, 416 will be a two-dimensional "flat" image. Therefore, any variation that occurs between the images will be based on the angle and on particular perspective visible along either of the planes 442, 444, 446. 3-D image reconstruction techniques may be used to emphasize the variation between the two images in creation of the 3-D representation.

The first, second, and third x-ray tube heads 412, 414, 416 may be fired at separate times, and in any sequence, and in response to specific positioning of the x-ray sensor 418, the x-ray unit 402, or positioning data obtained from a positioning sensor (not shown). For example, a positioning sensor may be provided in connection with a positioning guide, the sensor, the x-ray unit 402, or other components. A variety of automated logic controls such as provided by a controller may be used to provide accurate firing times and exposures of x-ray energy, and factor the specific angles or perspectives of the x-ray energy.

Although three x-ray tubes were depicted, it will be understood that two, four, or more x-ray tubes may be used. Images taken from at least two angles may provide basic information for a 3-D representation, but the inclusion of at least a third angle allows for additional 3-D information and correction to be provided. Thus, the use of a three- or more tube system may generate more 3-D information than a two-tube system.

In some embodiments, the convergence angle provided by the tube heads may be changed. Generally, the smaller angle would result in better detail, and less 3-D effects, whereas a larger angle would result in an enhanced 3-D nature but loss of detail. For example, in the use scenario of FIG. 4, the convergence angle may change by providing three hinges on the converging end of the tube heads to allow the x-ray generators to move in and out together. Additionally, the convergence angle and proper positioning may be automatically controlled by an image capture system. FIGS. 6A and 6B provide additional illustration on tube convergence configurations and operations.

In some embodiments, the x-ray tube heads may rotate to obtain enhanced 3-D data for a specific area of interest. Rotating the tube heads to change the positioning of the tubes may allow better visualization of certain structures and therefore the positioning of the images obtained from the tubes. For example, with a three-tube head configuration, the x-ray unit may be rotated between 0-120 degrees, allowing x-rays to be taken at every possible position of the tube heads.

As one example in a dental setting, x-ray images of teeth may be captured at a set angle of convergence, e.g., a 15 degree angulation. Three tube heads may be positioned, for example, around an intersecting axis 420 at 120 degrees from each other (as depicted in FIG. 4). The multiple tube heads may be rotated 120 degrees to reposition an x-ray tube from below the first axis 450 to above the first axis 450 (e.g., by rotating the entire set of multiple tube heads 412, 414, 416 clockwise or counterclockwise by 120 degrees). Such rotation (e.g., a 180 degree rotation) may be used to obtain x-rays of certain dental structures such as the canal and apex of a tooth root, or to obtain a better view of maxillary or mandibular teeth. Such rotation may also allow for two tube heads to be positioned at a given elevation (e.g., away from the crown and closer to the end of the tooth root).

Further, the multiple tube heads may be rotated to either "avoid" or gain a better 3-D rendering of the structure. Rotation may result in clearer images because of structures that block x-rays and cause a loss of information, for example, metal fillings, crowns, implants, posts, and cores. (X-ray blocking structures generally do not cause artifact problems such as occur in CT or cone-beam CT scans, but do result in the loss of information on the structures in front and behind). In some embodiments, information on the rotational position of the tube heads may be provided in connection with image processing to ensure correct processing of the DICOM images into a 3-D image.

Although the preceding examples illustrated the use of multiple x-ray tube heads, a single x-ray tube head having multiple collimators arranged to transmit x-ray energy at the angles or perspectives described herein may be used to provide a transmission of x-ray energy for producing images used in a 3-D representation. FIG. 5 provides an illustration of a use scenario 500 for an x-ray unit (not shown) having a single x-ray tube head with multiple internal collimators 512, 514, 516 used in connection with producing x-ray images for use in a three-dimensional radiographic representation in accordance with some embodiments.

In FIG. 5, triangulated x-ray energy is provided from multiple sources at a determined angle, similar to the use scenario 400 depicted in FIG. 4. As shown in FIG. 5, x-ray energy is transmitted along x-ray energy axes 532, 534, 536 originating from x-ray sources 502A, 502B, 502C within x-ray tube 510, with the angle of the x-ray energy axes 532, 534, 536 resulting from internal collimation from collimators 512, 514, 516 housed within x-ray tube 510. The x-ray energy is generated from x-ray generation units 506A, 506B, 506C, travels through collimating tubes 504A, 504B, 504C, and is collimated through each of the collimators 512, 514, 516 to result in transmissions of the x-ray energy from the x-ray tube 510 at an angle in the range of approximately 5-25 degrees from each other relative to the convergence point 522.

In some embodiments, a fused converging collimator unit may be provided to transmit x-ray energy at converging angles with each of the collimators 512, 514, 516. As illustrated, the collimators 512, 514, 516 may be located at the first end (e.g., the converging end) of a fused converging collimator unit (collectively 512, 514, 516), with the x-ray sources 502A, 502B, 502C provided at the opposite end of the fused converging collimator unit. The x-ray sources 502A, 502B, 502C may transmit x-ray energy respectively within a series of converging x-ray tubes 504A, 504B, 504C, for exit through the respective collimators 512, 514, 516.

The x-ray energy is received at the x-ray sensor 518 as it passes through or towards the convergence point 522. The x-ray sensor 518 may be located before, at, or after the convergence point 522. The position of the x-ray sensor 518 relative to the collimators 512, 514, 516 is determined in connection with a positioning guide 520 configured to receive or temporarily couple to the positioning guide 520. The positioning guide 520 may be coupled to a sensor holder 524 which holds the x-ray sensor 518 in place. Thus, with use of the positioning guide 520 and the sensor holder 524, a specific distance may be achieved relative to the convergence point 522, the x-ray sensor 518, the collimators 512, 514, 516, and the area of interest to be x-rayed. In one example setting useful with dentistry applications, the x-ray sensor 518 may be positioned for operation between 1 and 5 inches from the end of the x-ray tube 510.

The techniques previously described for the multiple x-ray tube use scenario 400 in FIG. 4 may also be applied in connection with the use scenario 500 in FIG. 5. Thus, the x-ray tube 510 in FIG. 5 may be configured to rotate between 0-120 degrees to allow enhanced views with rotation. Additionally, internal mechanisms may be provided to adjust the specific angle of collimation provided by collimators 512, 514, 516 relative to the convergence point 522. The x-ray energy provided by x-ray sources 502A, 502B, 502C may alternatively be provided from a single x-ray generator for all x-ray energy paths, or individual x-ray generators for each x-ray energy path as shown. Additional collimators may be provided within the x-ray tube 510 to focus or limit the transmission of x-ray energy. Moreover, two or four or more collimators may be provided within the x-ray tube 510 in a configuration similar to the one illustrated in FIG. 5 to allow additional focused x-ray transmissions towards a convergence point.

FIG. 6A provides an illustration of a series of round-shaped x-ray tubes 610, 620, 630 providing a configuration 600 that enables convergence of x-ray energy sources towards a center axis 640. The x-ray tubes 610, 620, 630 may be embodied as standalone x-ray tube heads (e.g., tube heads 412, 414, 416 in FIG. 4) or as x-ray tubes used in connection with internal collimation (e.g., collimating tubes 504A, 504B, 504C in FIG. 5).

The convergence of the x-ray energy sources may be provided to focus energy towards a convergence point at an area to be x-rayed located along the center axis 640 in accordance with some embodiments. In order for the x-ray tubes to converge towards the center axis 640, a portion of the housing of the x-ray tubes 610, 620, 630 is shaped to enable the interior space of the tube heads to overlap.

Specifically, FIG. 6A illustrates convergence through a series of cutout sections provided on each of the circular tubes 610, 620, 630. The cutout sections are arranged and sized to enable an overlapping of the interior space of a tube head with one or more other tube heads as the tubes converge towards the center axis 640. For example, as the angle of the tube 610 is changed to reduce the angle of projection of an x-ray beam as compared with the angle of projection of x-ray beams provided from the tubes 620, 630, the tube 610 converges to reduce the distance with the other x-ray tubes from the center axis 640. As the tube 610 moves, its cutout section(s) are configured to not interfere with the tubes 620 and 630 respectively. Providing this configuration for each of the tubes 610, 620, 630 enables the x-ray unit (or a fused converging collimator) to converge its energy transmission towards a much narrower angle, which may be used as the x-ray unit is positioned closer to or farther from the area of interest.

The tubes 610, 620, 630 may be configured to move in an opposite direction relative to the center axis 640 to perform separation. The convergence and the separation of the x-ray tubes towards and from the center axis 640 or relative to a convergence axis may be controlled and related to the precise distance and angle relative to the area of interest receiving the x-ray energy, which may be determined by the proximity of the x-ray unit to the area of interest. For example, as the x-ray unit is positioned farther away from a digital x-ray sensor, the tubes 610, 620, 630 may be configured to spread apart to maintain the fixed angle towards the x-ray energy convergence point or an area of interest. Likewise, as the x-ray unit is positioned closer to the digital x-ray sensor, the tubes may be configured to converge and move closer to each other to maintain the fixed angle towards the convergence point.

FIG. 6B provides an illustration of a series of rectangular-shaped tubes 652, 654, 656 providing a configuration 650 for converging towards a center axis 660 in accordance with some embodiments. The rectangular shaped tubes 652, 654, 656 may be arranged to enable movement of the individual tubes relative to various axes. For example, the convergence may be used to maintain a 120 degree separation between tubes 652, 654, 656, and maintain equal angle and spacing relationships among the tubes 652, 654, 656.

As illustrated, the x-ray tube 652 may be configured for movement in a first direction 662; the x-ray tube 654 may be configured for movement in a second direction 664; and the x-ray tube 656 may be configured for movement in a third direction 666. Similar to the separation and convergence operations described in FIG. 6A, the x-ray tubes may be configured to separate or converge at 120 degrees from each other. Thus, as the x-ray tubes converge in directions 662, 664, 666 of movement, the distance between the x-ray tubes 652, 654, 656 relative to axis 660 decreases; whereas as the x-ray tubes separate in directions 662, 664, 666 of movement, the distance between the x-ray tubes 652, 654, 656 relative to axis 660 increases. For example, the directions 662, 664, 666 of movement may be in relation to a proximity sensor.

In some scenarios, use of rectangular tube heads may also enable reduced exposure to x-rays to a human, animal, or object because the shape of the sensor receptor may be generally the same shape and size. A rectangular collimator provided in the tube head may be smaller than corresponding round tube collimators. With use of a rectangular x-ray source, there may be more "cone cuts", e.g., alignment mistakes resulting in the x-ray energy missing a portion of the sensor. Due to the increased difficulty of alignment of rectangular collimation, rectangular tubes may be arranged and properly positioned with a position guide to prevent cone cuts from improper alignment with the sensor.

A round tube head scheme may be used for the distinct capture of maxillary versus mandibular teeth views in dental settings, because certain rotated rectangular configurations may not provide the same orientation with regard to the rectangular sensor. Alternatively, a rectangular configuration may provide a full 180 degree rotation of the tube heads, and a positioning guide to align the horizontal bottom of the tube heads with the horizontal bottom of the sensor. Round tubes may not present this alignment issue due to their round nature, but rotational alignment or positioning with the x-ray sensor may assist in the 3-D reconstruction of the image. Various positioning components and techniques may be used to address such use scenarios.

The present techniques also may be used in connection with various collimation techniques and x-ray positioning systems to reduce cone cuts and unneeded radiation exposure. One such x-ray positioning system that may be used in conjunction with the presently described techniques is the HealthFirst TRU-ALIGN® Laser-Aligning X-Ray Positioning System, which may attach to the end of a round x-ray tube to provide a rectangular collimation of transmitted x-ray energy based on the shape of the sensor. In alternative embodiments, collimation techniques may also be integrated into the x-ray tube head itself, for example by providing rectangular collimation at the opening end of the tube in addition to the internal collimation.

Consistent with the techniques previously described, as an alternative to the converging x-ray tube heads depicted in FIGS. 6A and 6B, a series of x-ray tube heads could be set in a fixed angle and/or fixed distance apart for use in capturing images for the 3-D representation. The proper positioning (e.g., distance) of the x-ray source would still need to be achieved, however. This might be accomplished through x-ray capture operations that position the x-ray source at the same focal distance on every shot, or the use of a position sensor and indicator to determine when x-ray tube heads are at an optimal distance from the x-ray sensor.

In the illustration of FIGS. 4 and 5, the particular angle relative to, and the convergence of x-ray energy towards, the convergence point (such as convergence point 422, 522) from a plurality of x-ray tube heads is based on the distance that the x-ray unit (such as x-ray unit 402 of FIG. 4) is positioned from the convergence point. In a further embodiment, an x-ray unit may be configured to provide automatic adjustment of angles using self-adjusting x-ray tube heads or collimating units, to enable the x-ray unit to capture images at a determined angle regardless of the position from the convergence point, without requiring the object of interest or the x-ray unit to move.

For example, as the x-ray unit is moved closer to the imaging sensor, the angle between the tube heads may be increased to maintain the determined angle relative to the convergence point. Likewise, as an x-ray tube head is moved away from the x-ray sensor, the angle between the tube heads may be decreased to maintain the determined angle relative to the convergence point or other point of interest. The angles of the x-ray tube may be adjusted to keep the sensor "on target" as the distance to the sensor from the x-ray tube heads is increased or decreased. Positioning sensors may be used to direct the operator to correctly align the tube head with the sensor. For example, audible and/or visible directions or indicators may be used to assist an operator to obtain a correct image with correct angulation, and to avoid cone cuts. Such use of positioning sensors may also reduce the need for retakes and un-necessary radiation.

As a further example, a set of x-ray tubes, whether mounted in a horizontal or vertical "triangular" position, may be configured to converge or move apart as the tube heads move closer or farther away from the convergence point. This may be performed in connection with sensing techniques used to determine the position of the x-ray unit, and whether the x-ray unit is moved closer or farther away from the convergence point. One such sensing technique may be accomplished with a positioning or proximity sensor such as a sensor operably coupled to the x-ray sensor (e.g., an intra-oral x-ray sensor) used for distance sensing and alignment of the x-ray unit and its tube heads.

In some embodiments, a horizontal or vertically aligned configuration of x-ray sources may be used instead of a triangulated configuration. For example, three or more x-ray sources may be aligned side-by-side along an axis (such as being located parallel to a substantially horizontal or substantially vertical axis relative to the area or object of interest). The three or more x-ray sources may converge together along the horizontal plane, for example. Such a side-by-side configuration may be incorporated into separate tubes (such as shown in FIG. 4) or in an internal collimation configuration (such as shown in FIG. 5) having one tube opening unit.

In some embodiments, the particular distance of x-ray energy emission from the x-ray unit between or among the individual x-ray tube heads may change based on the x-ray tube head distance from the sensor, using a proximity sensor to obtain positioning information. Positioning information (containing information values such as angle, distance, and other determined position information) of the particular x-ray image captures may be provided to the processing rendering software that combines the 2-D images into 3-D images.

In another embodiment, the configuration may be arranged to maintain a "fixed" angle between the grouped x-ray tube heads, for example using the configuration of three x-ray tube heads depicted in FIG. 4. The determined angle to be maintained may be, for example, 15 degrees relative to the convergence point. Mechanisms may be provided to move the tube heads laterally (in and out), as all three tube heads move apart or together equally to maintain the same angles between all tube heads. For example, this mechanism may be automatically provided as the x-ray unit is moved closer or farther away from the x-ray sensor, to maintain the determined angle relative to the convergence point.

Implementing a set of fixed angles relative to an area of interest being x-rayed with tube heads that move automatically to maintain the fixed angles relative to a convergence point, may be provided to enable simplified processing and perspective of data in a 3-D representation. This may allow the software to use the same angle and same algorithm to produce all image data in the 3-D representations, without needing a special connection to, or positioning data from, the x-ray tube head unit. In other embodiments, however, positioning information of the x-ray source and x-ray tube units used to obtain the particular x-ray images may be factored by the 3-D processing and rendering environment.

Thus, the x-ray tube structures provided by an x-ray unit may be adapted to converge towards an axis of interest, and otherwise reduce inter-tube distance in order to focus towards a location of interest as the x-ray unit is moved closer to the location of interest (e.g., by providing "fused" tube units). Convergence of the x-ray tube structures may be performed in connection with any number of automated or manual techniques, and with or without the use of a proximity sensor or computing system. Such techniques may be used to calculate the precise angle to determine the convergence point or position, in order to determine the appropriate angle of interest for individual or groups of x-ray tube units or collimators.

Other configurations such as an automated movement of a single x-ray unit adapted to perform separate transmissions of the x-ray energy may also be provided in connection with the presently described embodiments. Such imaging capture may be used, for example, with imaging of stationary objects.

Figure 7:
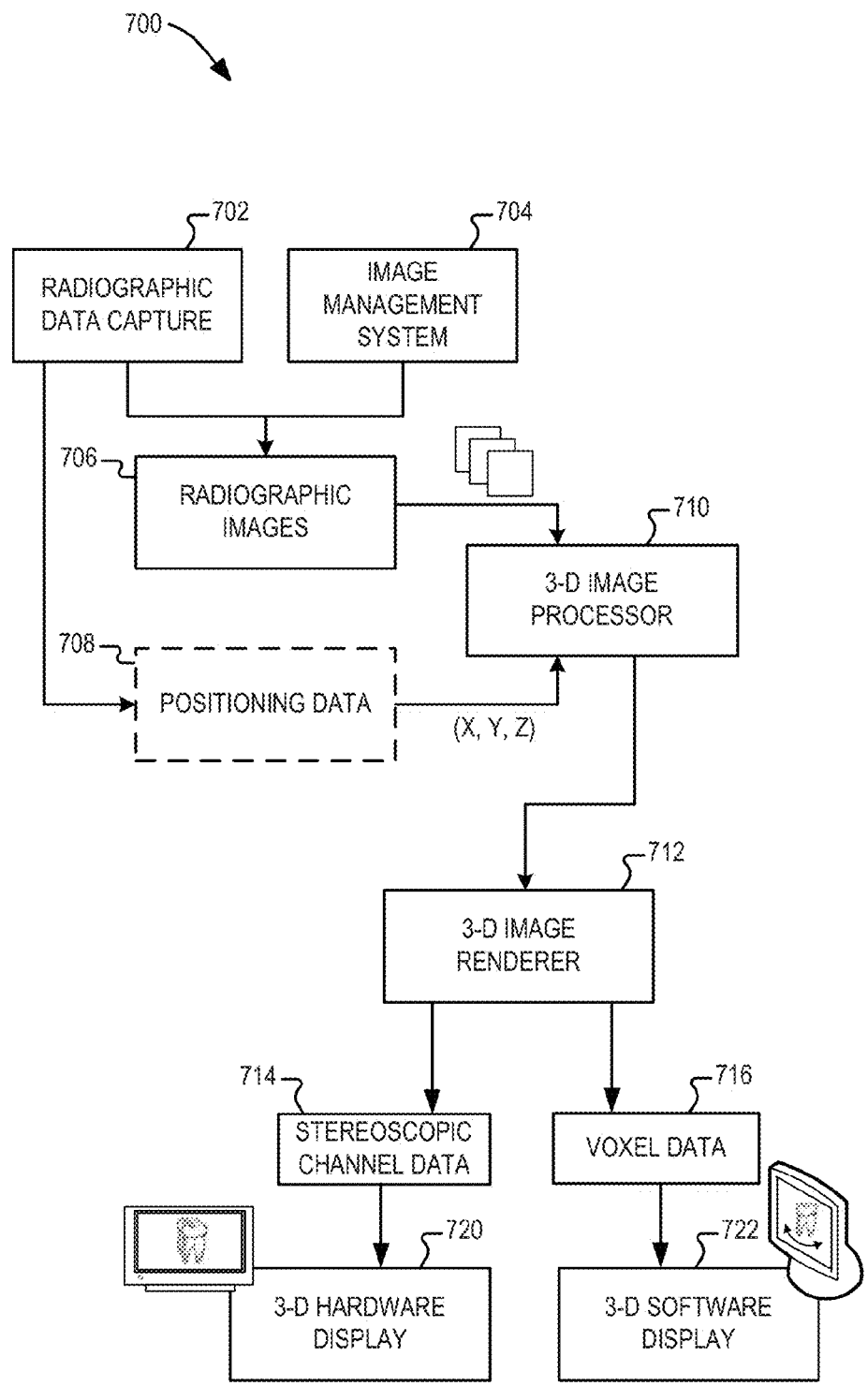
FIG. 7 is an illustration of data flow in an image processing system used for creating and displaying a three-dimensional radiographic representation in accordance with some embodiments.

FIG. 7 provides an illustration of data flow 700 occurring in an image processing system used for creating and displaying a three-dimensional radiographic representation in accordance with some embodiments. The data needed for display of the three-dimensional radiographic representation in the data flow 700 is facilitated by use of a 3-D image processor 710 and a 3-D image renderer 712. Radiographic data is provided to each of these components to create and compile the three-dimensional radiographic representation.

As illustrated, data from either or both of a radiographic data capture 702 or an image management system 704 are used to provide a set of radiographic images 706. The radiographic data capture 702 may also provide positioning data 708 for the radiographic images 706 such as image capture coordinates or other image-specific positioning values. The positioning data 708 may include data related to the perspective of the x-ray image capture, including the angle differences between the various images, the distance of the image capture, and the like. Alternatively, the positioning data 708 may be provided in metadata or another data indication that is stored directly in or accompanying the radiographic images 706 or a transmission of the radiographic images 706. In some embodiments, in connection with fixed-angle or position-guided uses, the positioning data is used for generating the 3-D representation. For example, Positioning data 708 may be used in some scenarios to determine the rotation orientation of the tube heads, or other environmental or positioning information for use in creation of the 3-D representation reconstruction.

The 3-D image processor 710 may process the radiographic images 706 and positioning data 708 for creation of a 3-D image representation. For example, this may include selecting some or all of the 2-D images from a plurality of available images for use in the 3-D image representation. This may also include extracting relevant information from the radiographic images 706 or the positioning data 708 to determine which 2-D images may be combined. The 3-D image processor 710 may also receive and process user input, for example, to generate a 3-D representation of a particular area or to change the characteristics of an existing 3-D representation.

The 3-D image renderer 712 may then produce a 3-D image representation in a format appropriate for display, using any number of 3-D general and specialized graphic rendering techniques. For example, the 3-D image renderer 712 may produce stereoscopic channel data 714 used in connection with a 3-D hardware display 720. In another example, the 3-D image renderer 712 may produce volumetric pixel (voxel) data 716 used in connection with a 3-D software environment, for example a software display allowing user interaction. The 3-D image renderer 712 may operate to provide various three-dimensional effects such as depth of field.

The software would allow viewing of individual tube images or as a combined 3-D representation. For example, in a software environment provided by a 3-D software display 722, rather than requiring two images to be viewed stereoscopically with stereoscopic vision, the computer may generate a 3-D model, which can be viewed on a 2-D screen. The 3-D model may provide the ability to rotate and change perspective of a displayed image or series of images. A 3-D model provided in a software environment may provide the ability to navigate in a virtual space to show the true 3-D nature of the structure, similar to computer assisted imaging techniques produced with 3-D photography and computer-aided design (CAD) in products such as CEREC (Chairside Economical Restoration of Esthetic Ceramics), which allow users to see 3-D views of teeth and models.

The 3-D representation may also be viewed on a stereoscopic screen provided by a 3-D hardware display 720. Although the representation is a 3-D generated model using a series of images relative to determined angles (triangulation) to produce the 3-D representation, portions of the 3-D representation (e.g., images being generated from the combined 3-D model representation) may be output in a set of stereoscopic side-by-side images. Additional images taken from additional angles may be used to provide more resolution, correction, and information for use in the 3-D representation. For example, images from multiple areas may be combined into a larger 3-D image of an area of interest. For example, providing a 3-D model of structures such as teeth, bones, and other dental structures to produce a model similar to CT/Cone Beam CT, may allow use of x-ray imaging offering lower radiation, in place of CT/Cone Beam CT for implant planning and placement where the exact position of sinuses and nerves need to be known in 3-D.

Figure 8:
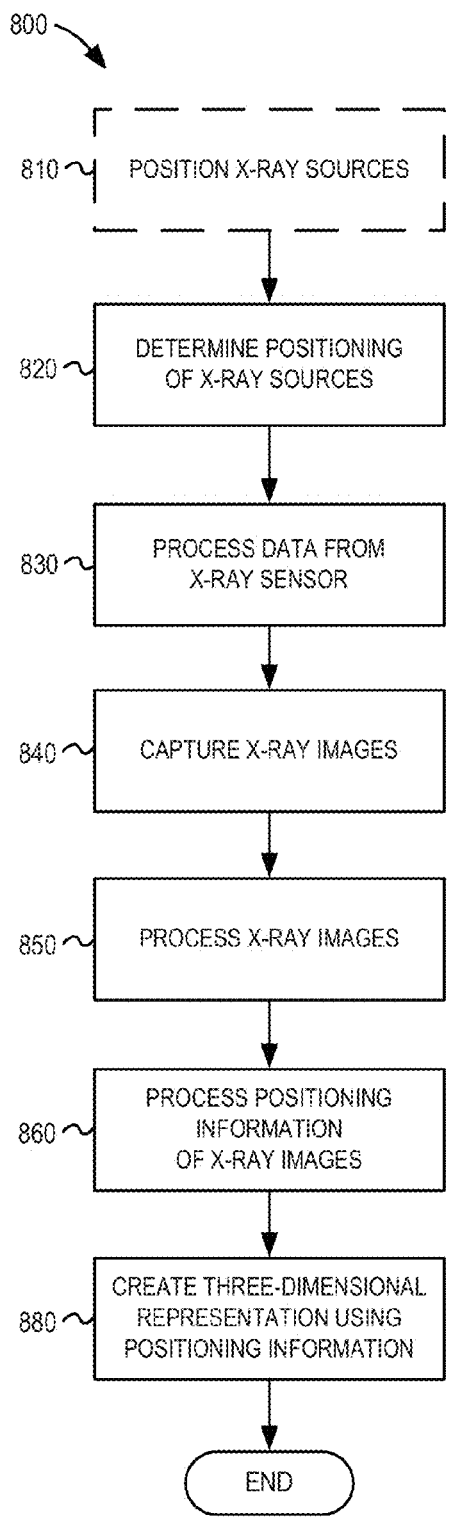
FIG. 8 is a flowchart depicting a method for creating and processing three-dimensional radiographic representations in accordance with some embodiments.

FIG. 8 provides an illustration of a flowchart 800 configured for creating and processing three-dimensional radiographic representations in accordance with some embodiments. As shown for use in some embodiments, a series of operations 810-880 are performed in sequence to result in a three-dimensional representation of a series of two-dimensional x-ray images. It will be understood that the series of operations 810-880 may be performed in an alternate sequence, and various operations may be omitted, substituted, and added.

First, one or more x-ray sources may be positioned (operation 810), relative to an area of interest to be x-rayed on a human, animal, or object. The positioning of x-ray source may be determined (operation 820), for example using a positioning sensor provided by a digital x-ray sensor, or through the use of a positioning guide. Determining the positioning of the x-ray source may provide feedback to re-position the x-ray sources (operation 810) or collimators used in connection with the x-ray sources. In some embodiments, positioning of the x-ray sources is optional if a fixed position or angle is provided for the convergence point and the x-ray source.

As x-ray energy is transferred from the one or more x-ray sources to the x-ray sensor, the x-ray sensor will receive the x-ray energy. The data from the x-ray sensor is processed (operation 830) to obtain digital data. The digital data may then be used to capture the respective x-ray images (operation 840).

After capture of the respective x-ray images, the respective x-ray images are processed (operation 850). Before, concurrently, or after the processing of the respective x-ray images, the positioning information of the respective x-ray images is processed (operation 860). This positioning information may be provided directly within the respective x-ray images, or from data from a positioning sensor (for example, obtained in connection with operation 820).

A three-dimensional representation of the respective x-ray images may be created using the processed positioning information (operation 880). The three-dimensional representation may be displayed using any combination of the 3-D rendering, visualization, and display techniques described herein or as known in the art.

Although the proceeding examples were provided with reference to various 3-D applications, an x-ray unit or system providing multiple x-ray heads may be configured for use in both 3-D and 2-D imaging settings. For example, the x-ray unit could be used as a "traditional" x-ray with only one x-ray generator firing or as a 3-D system using all the x-ray generators (firing in series) as the operator requires.

Uses of non-digital x-ray equipment and techniques may also be incorporated in connection with the techniques and configurations described herein. For example, an x-ray processing configuration which captures images using film and obtains a digital image using a scan of the exposed film may also be adapted in connection with the three-dimensional representation techniques disclosed herein. As another example, an x-ray processing configuration may be used to process digital copies of previously captured x-ray images from film-based systems and devices taken at known perspectives and angles.

Other medical settings may also apply the x-ray capture and display techniques and configurations described herein. These may include tissue and skeletal x-rays, including in specialized settings such as mammography. Further, although some of the preceding examples were provided with reference to dental medical settings, it will be understood that a variety of other uses may be provided with three-dimensional triangulation x-ray imaging. These may include security applications, industrial applications, commercial applications, and other general uses where radiographic images are produced and analyzed.

Additionally, although various dental equipment, dental x-ray units and systems, and medical radiological processing systems were described in the present disclosure, such systems were provided for purposes of example. A variety of modifications may be made in connection with the configurations and techniques described herein to provide applicability to other commercial, industrial, scientific, and medical settings.

Figure 9:
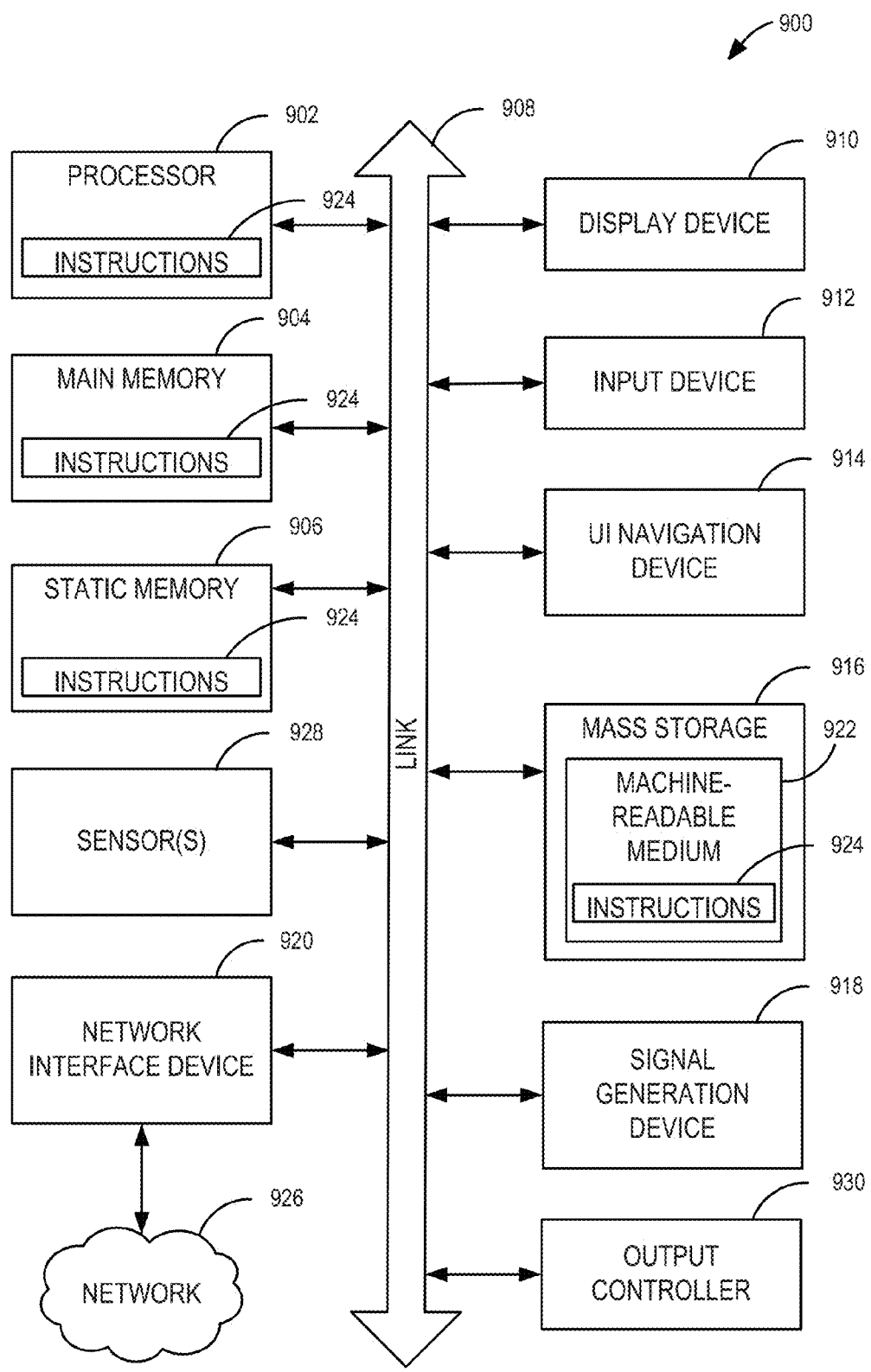
FIG. 9 is a block diagram of architecture for an example computing system used in accordance with some embodiments.

FIG. 9 is a block diagram illustrating an example computer system machine upon which any one or more of the three-dimensional rendering techniques herein discussed may be performed. Computer system 900 specifically may be used as an image processing or management system, or provide an example of any other electronic control or computing platform described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a Personal Digital Assistant (PDA), a mobile telephone, a web appliance, a network-connected terminal, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 900 includes a processor 902 (e.g., a central processing unit (CPU), a graphics processing unit (GPU) or both), a main memory 904 and a static memory 906, which communicate with each other via an interconnect 908 (e.g., a link, a bus, etc.). The computer system 900 may further include a video display device 910, an alphanumeric input device 912 (e.g., a keyboard), and a user interface (UI) navigation device 914 (e.g., a mouse). In some embodiments, the video display device 910, input device 912 and UI navigation device 914 are a touch screen display. The computer system 900 may additionally include a storage device 916 (e.g., a drive unit), a signal generation device 918 (e.g., a speaker), a network interface device 920 (which may include or operably communicate with one or more antennas, transceivers, or other wireless communications hardware), and one or more sensors 928, such as a global positioning system (GPS) sensor, compass, accelerometer, or other sensor.

The storage device 916 may include a machine-readable medium 922 on which is stored one or more sets of data structures or instructions 924 (e.g., software) embodying or utilized by any one or more of the methodologies or functions described herein. The instructions 924 may also reside, completely or at least partially, within the main memory 904, static memory 906, and/or within the processor 902 during execution thereof by the computer system 900, with the main memory 904, static memory 906, and the processor 902 also constituting machine-readable media.

While the machine-readable medium 922 is illustrated in an example embodiment to be a single medium, the term "machine-readable medium" may include a single medium or multiple media (e.g., a centralized or distributed database, and/or associated caches and servers) that store the one or more instructions 924. The term "machine-readable medium" shall also be taken to include any tangible medium that is capable of storing, encoding or carrying instructions for execution by the computer system 900 and that cause the computer system 900 to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 924 may further be transmitted or received over a communications network 926 using a transmission medium via the network interface device 920 utilizing any one of a number of well-known transfer protocols (e.g., frame relay, internet protocol (IP), transmission control protocol (TCP), user datagram protocol (UDP), hypertext transfer protocol (HTTP)). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the computer system 900, and includes digital or analog communications signals or other intangible medium to facilitate communication of such software.

As an additional example, computing embodiments described herein may be implemented in one or a combination of hardware, firmware, and software. Embodiments may also be implemented as instructions stored on a computer-readable storage device, which may be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media.

It should be understood that the functional units or capabilities described in this specification may have been referred to or labeled as components or modules, in order to more particularly emphasize their implementation independence. Components or modules may be implemented in any combination of hardware circuits, programmable hardware devices, and other discrete components. Components or modules may also be implemented in software for execution by various types of processors. An identified component or module of executable code may, for instance, comprise one or more physical or logical blocks of computer instructions, which may, for instance, be organized as an object, procedure, or function. Nevertheless, the executables of an identified component or module need not be physically located together, but may comprise disparate instructions stored in different locations which, when joined logically together, comprise the component or module and achieve the stated purpose for the component or module. Indeed, a component or module of executable code may be a single instruction, or many instructions, and may even be distributed over several different code segments, among different programs, and across several memory devices. Similarly, operational data may be identified and illustrated herein within components or modules, and may be embodied in any suitable form and organized within any suitable type of data structure. The operational data may be collected as a single data set, or may be distributed over different locations including over different storage devices, and may exist, at least partially, merely as electronic signals on a system or network. The components or modules may be passive or active, including agents operable to perform desired functions.

Additional examples of the presently described method, system, and device embodiments include the following, non-limiting configurations. Each of the following non-limiting examples may stand on its own, or may be combined in any permutation or combination with any one or more of the other examples provided below or throughout the present disclosure.

Example 1 can include subject matter (such as an apparatus, a method, a means for performing acts, or a machine-readable medium including instructions that, when performed by the machine, can cause the machine to perform acts), to provide a method for creating a three-dimensional radiographic representation, comprising: processing a set of x-ray images obtained at a same x-ray sensor from multiple x-ray transmissions, the multiple x-ray transmissions being provided by one or more x-ray sources, and the multiple x-ray transmissions arranged at a set of converging angles relative to a convergence point in the path of the multiple x-ray transmissions; processing positioning information for the set of x-ray images, the positioning information indicating the set of converging angles; and creating a three-dimensional radiographic representation from the set of x-ray images based on the set of converging angles indicated from the positioning information.

Example 2 can include, or can optionally be combined with the subject matter of Example 1 to optionally include, controlling a capture of the set of x-ray images by controlling the multiple x-ray transmissions being provided by the one or more x-ray sources to the same x-ray sensor, wherein the one or more x-ray sources include three x-ray sources arranged in a triangulated configuration.

Example 3 can include, or can optionally be combined with the subject matter of one or any combination of Examples 1 or 2 to optionally include, positioning the three x-ray sources to emit x-ray energy at the set of converging angles, wherein the converging angles are provided to cause the multiple x-ray transmissions to converge at the convergence point.

Example 4 can include, or can optionally be combined with the subject matter of one or any combination of Examples 1 through 3 to optionally include, determining the positioning for the three x-ray sources to emit x-ray energy at the set of converging angles, wherein positioning the three or more x-ray sources includes using the determined positioning.

Example 5 can include, or can optionally be combined with the subject matter of one or any combination of Examples 1 through 4 to optionally include, the same x-ray sensor being positioned in the path of the multiple x-ray transmissions at or before the convergence point.

Example 6 can include, or can optionally be combined with the subject matter of one or any combination of Examples 1 through 5 to optionally include, processing the set of x-ray images obtained at the same x-ray sensor from the multiple x-ray transmissions including: capturing digital data received at the same x-ray sensor from the multiple x-ray transmissions, wherein the same x-ray sensor is a digital x-ray sensor; and processing the digital data to create the set of x-ray images.

Example 7 can include, or can optionally be combined with the subject matter of one or any combination of Examples 1 through 6 to optionally include, obtaining the set of x-ray images from an image data store.

Example 8 can include, or can optionally be combined with the subject matter of one or any combination of Examples 1 through 7 to optionally include, providing the three-dimensional radiographic representation as a three-dimensional virtual model for display in a software user interface, wherein the software user interface enables rendering and navigation of the three-dimensional virtual model in a virtual environment displayed on a two-dimensional display unit.

Example 9 can include, or can optionally be combined with the subject matter of one or any combination of Examples 1 through 8 to optionally include, generating voxel data for the three-dimensional virtual model for display in the virtual environment enabled by the software user interface.

Example 10 can include, or can optionally be combined with the subject matter of one or any combination of Examples 1 through 9 to optionally include, providing the three-dimensional radiographic representation for display on a stereoscopic display unit, and generating two offset channels for display on the stereoscopic display unit, wherein the stereoscopic display unit is configured to display the two offset channels from the three-dimensional radiographic representation for three-dimensional perception by a human.

Example 11 can include, or can optionally be combined with the subject matter of one or any combination of Examples 1-10 to include, subject matter (such as an apparatus, a method, a means for performing acts, or a machine-readable medium including instructions that, when performed by the machine, that can cause the machine to perform acts), such as can include an x-ray device, comprising: three or more x-ray sources positioned to emit x-ray energy towards a convergence point, the three or more x-ray sources being angled at a set of one or more determined angles relative to the convergence point to emit the x-ray energy at the set of determined angles, wherein the convergence point is located at a convergence of a path of the x-ray energy emitted from the three or more x-ray sources; wherein the x-ray device is operable at a fixed location to emit x-ray energy from the three or more x-ray sources at respective times for receiving at a digital x-ray sensor.

Example 12 can include, or can optionally be combined with the subject matter of Example 11 to optionally include, the three or more x-ray sources comprising three x-ray tube units arranged in a triangular configuration including a first x-ray tube unit and a second x-ray tube unit positioned along a first axis, and a third x-ray tube unit positioned along a second axis, the second axis parallel to the first axis and intersecting the first axis at a point located between the first x-ray tube unit and the second-ray tube unit.

Example 13 can include, or can optionally be combined with the subject matter of one or any combination of Examples 11 through 12 to optionally include, the three or more x-ray sources comprising three x-ray tube units arranged in a parallel configuration, including a first x-ray tube unit, a second x-ray tube unit, and a third x-ray tube unit positioned parallel to an axis.

Example 14 can include, or can optionally be combined with the subject matter of one or any combination of Examples 11 through 13 to optionally include, the three or more x-ray sources comprising three x-ray collimators housed in a same x-ray tube unit, the three x-ray collimators being arranged in a triangular configuration including a first x-ray collimator and a second x-ray collimator positioned along a first axis, and a third x-ray collimator positioned along a second axis, the second axis parallel to the first axis and intersecting the first axis at a point located between the first x-ray collimator and the second x-ray collimator.

Example 15 can include, or can optionally be combined with the subject matter of one or any combination of Examples 11 through 14 to optionally include, the digital x-ray device being further configured to change an orientation of the three or more x-ray sources relative to the set of determined angles, and to rotate a positioning of the three or more x-ray sources relative to the digital x-ray sensor.

Example 16 can include, or can optionally be combined with the subject matter of one or any combination of Examples 1-15 to include, subject matter (such as an apparatus, a method, a means for performing acts, or a machine-readable medium including instructions that, when performed by the machine, that can cause the machine to perform acts), such as can include a three-dimensional radiographic imaging system, comprising: multiple x-ray sources configured to emit x-ray energy towards a convergence point with respective x-ray beams, wherein the x-ray sources are arranged at a set of determined angles relative to the convergence point to transmit the respective x-ray beams at the set of determined angles; an x-ray sensor arranged to receive the x-ray energy from the respective x-ray beams, the x-ray sensor configured to produce one or more digital signals providing data for radiographic images from the respective x-ray beams, wherein the radiographic images provide varying perspectives based on the set of determined angles; and an image processing system configured to combine the radiographic images into a three-dimensional representation based on the varying perspectives provided by the radiographic images.

Example 17 can include, or can optionally be combined with the subject matter of Example 16 to optionally include, the multiple x-ray sources including three x-ray sources, including a first x-ray source and a second x-ray source located substantially perpendicular to a first axis, and a third x-ray source located substantially parallel to the first axis; wherein each of the first x-ray source, the second x-ray source, and the third x-ray source are arranged to emit the x-ray energy to the convergence point at the set of determined angles.

Example 18 can include, or can optionally be combined with the subject matter of one or any combination of Examples 16 through 17 to optionally include, a positioning sensor, the positioning sensor configured to determine an indication of positioning of the multiple x-ray sources relative to the x-ray sensor.

Example 19 can include, or can optionally be combined with the subject matter of one or any combination of Examples 16 through 18 to optionally include, the determined angles of one or more of the multiple x-ray sources relative to the convergence point being automatically changed based on a changed proximity of the one or more of the multiple x-ray sources relative to the x-ray sensor, the proximity determined at least in part by the positioning sensor.

Example 20 can include, or can optionally be combined with the subject matter of one or any combination of Examples 16 through 19 to optionally include, the multiple x-ray sources including three x-ray sources, including a first x-ray source and a second x-ray source located substantially perpendicular to a first axis, and a third x-ray source located substantially parallel to the first axis; wherein the first x-ray source, the second x-ray source, and the third x-ray source converge as the multiple x-ray sources are positioned closer to the x-ray sensor, and separate as the multiple x-ray sources are positioned further away from the x-ray sensor, wherein positioning relative to the x-ray sensor is determined at least in part by the positioning sensor.

Example 21 can include, or can optionally be combined with the subject matter of one or any combination of Examples 16 through 20 to optionally include, a display configured to render the three-dimensional representation based on the set of determined angles.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. A method for providing a three-dimensional radiographic representation, comprising:
    processing a set of x-ray images providing various perspectives, the x-ray images obtained at a same x-ray sensor from multiple x-ray transmissions, the multiple x-ray transmissions being provided by one or more x-ray sources, and the multiple x-ray transmissions arranged at a set of converging angles relative to a convergence point in the path of the multiple x-ray transmissions, wherein the multiple x-ray transmissions include three x-ray transmissions that are emitted from the one or more x-ray sources in a triangulated configuration relative to the x-ray sensor, the three x-ray transmissions originating from two locations on a first axis and one location on a second axis, wherein the first axis is substantially perpendicular to the second axis;

processing positioning information for the set of x-ray images, the positioning information indicating the set of converging angles of the triangulated configuration from the two locations on the first axis and the one location on the second axis relative to the convergence point; and creating a three-dimensional radiographic representation from the set of x-ray images based on the set of converging angles of the triangulated configuration indicated from the positioning information.

2. The method of claim 1, further comprising:

controlling a capture of the set of x-ray images by controlling the multiple x-ray transmissions being provided by the one or more x-ray sources to the same x-ray sensor, wherein the one or more x-ray sources include three x-ray sources arranged in the triangulated configuration.

3. The method of claim 2, further comprising:

positioning the three x-ray sources to emit x-ray energy at the set of converging angles, wherein the converging angles are provided to cause the multiple x-ray transmissions to converge at the convergence point.

4. The method of claim 3, further comprising:

determining the positioning for the three x-ray sources to emit x-ray energy at the set of converging angles, wherein positioning the three x-ray sources includes using the determined positioning.

5. The method of claim 1, wherein the same x-ray sensor is positioned in the path of the multiple x-ray transmissions at or before the convergence point.

6. The method of claim 1, wherein processing the set of x-ray images obtained at the same x-ray sensor from the multiple x-ray transmissions includes:

capturing digital data received at the same x-ray sensor from the multiple x-ray transmissions, wherein the same x-ray sensor is a digital x-ray sensor; and processing the digital data to create the set of x-ray images.

7. The method of claim 1, further comprising:

obtaining the set of x-ray images from an image data store.

8. The method of claim 1, further comprising providing the three-dimensional radiographic representation as a three-dimensional virtual model for display in a software user interface, wherein the software user interface enables rendering and navigation of the three-dimensional virtual model in a virtual environment displayed on a two-dimensional display unit.

9. The method of claim 8, further comprising generating voxel data for the three-dimensional virtual model for display in the virtual environment enabled by the software user interface.

10. The method of claim 1, further comprising providing the three-dimensional radiographic representation for display on a stereoscopic display unit, and generating two offset channels for display on the stereoscopic display unit, wherein the stereoscopic display unit is configured to display the two offset channels from the three-dimensional radiographic representation for three-dimensional perception by a human.

11. An x-ray device, comprising:

three or more x-ray sources positioned to emit x-ray energy with multiple x-ray transmissions towards a convergence point, the three or more x-ray sources being angled at a set of one or more determined angles relative to the convergence point to emit the x-ray energy at the set of determined angles, wherein the convergence point is located at a convergence of a path of the x-ray energy emitted from the three or more x-ray sources, wherein the multiple x-ray transmissions include three x-ray transmissions that are emitted from the three or more x-ray sources in a triangulated configuration relative to a positioned digital x-ray sensor, the three x-ray transmissions originating from two locations on a first axis and one location on a second axis, wherein the first axis is substantially perpendicular to the second axis; and a positioning component configured to provide positioning information for x-ray images captured with the positioned digital x-ray sensor, the x-ray images providing various perspectives relative to the positioned digital x-ray sensor, and the positioning information indicating the set of converging angles of the triangulated configuration from the two locations on the first axis and the one location on the second axis relative to the convergence point;

wherein the x-ray device is operable at a fixed location to emit x-ray energy from the three or more x-ray sources at respective times for receiving at the positioned digital x-ray sensor, and wherein the positioning information for the x-ray images is useable for creating a three-dimensional radiographic representation from the x-ray images based on the set of converging angles of the triangulated configuration indicated from the positioning information.

12. The x-ray device of claim 11, wherein the three or more x-ray sources comprise three x-ray tube units arranged in the triangular configuration including a first x-ray tube unit and a second x-ray tube unit positioned along the first axis, and a third x-ray tube unit positioned along the second axis, the second axis intersecting the first axis at a point located between the first x-ray tube unit and the second-ray tube unit.

13. The x-ray device of claim 11, wherein the three or more x-ray sources comprise three x-ray collimators housed in a same x-ray tube unit, the three x-ray collimators being arranged in the triangular configuration including a first x-ray collimator and a second x-ray collimator positioned along the first axis, and a third x-ray collimator positioned along the second axis, the second axis and intersecting the first axis at a point located between the first x-ray collimator and the second x-ray collimator.

14. The x-ray device of claim 11, wherein the x-ray device is further configured to change an orientation of the three or more x-ray sources relative to the set of determined angles, and to rotate a positioning of the three or more x-ray sources relative to the digital x-ray sensor.

15. A three-dimensional radiographic imaging system, comprising:

multiple x-ray sources configured to emit x-ray energy towards a convergence point located in the path of respective x-ray beams, wherein the x-ray sources are arranged at a set of determined angles relative to the convergence point to transmit the respective x-ray beams at a set of converging angles;

an x-ray sensor arranged to receive the x-ray energy from the respective x-ray beams, the x-ray sensor configured to produce one or more digital signals providing data for x-ray images from the respective x-ray beams, wherein the x-ray images provide varying perspectives based on the set of converging angles; and an image processing system configured to combine the x-ray images into a three-dimensional representation based on the varying perspectives provided by the radiographic images by:
processing the x-ray images obtained at the x-ray sensor from the respective x-ray beams, wherein the multiple x-ray transmissions include three x-ray transmissions that are emitted from the multiple x-ray sources in a triangulated configuration relative to the x-ray sensor, the three x-ray transmissions originating from two locations on a first axis and one location on a second axis, wherein the first axis is substantially perpendicular to the second axis;
processing positioning information for the x-ray images, the positioning information indicating the set of converging angles of the triangulated configuration from the two locations on the first axis and the one location on the second axis relative to the convergence point; and
creating the three-dimensional representation from the x-ray images based on the set of converging angles of the triangulated configuration indicated from the positioning information.

16. The three-dimensional radiographic imaging system of claim 15,
wherein the multiple x-ray sources include three x-ray sources, including a first x-ray source and a second x-ray source located along the first axis, and a third x-ray source located along the second axis; and
wherein each of the first x-ray source, the second x-ray source, and the third x-ray source are arranged to emit the x-ray energy to the convergence point at the set of converging angles.

17. The three-dimensional radiographic imaging system of claim 15, further comprising:
a positioning sensor, the positioning sensor configured to determine an indication of positioning of the multiple x-ray sources relative to the x-ray sensor.

18. The three-dimensional radiographic imaging system of claim 17, wherein the determined angles of one or more of the multiple x-ray sources relative to the convergence point are automatically changed based on a changed proximity of the one or more of the multiple x-ray sources relative to the x-ray sensor, the proximity determined at least in part by the positioning sensor.

19. The three-dimensional radiographic imaging system of claim 17,
wherein the multiple x-ray sources include three x-ray sources, including a first x-ray source and a second x-ray source located along the first axis, and a third x-ray source located along the second axis; and
wherein the first x-ray source, the second x-ray source, and the third x-ray source converge as the multiple x-ray sources are positioned closer to the x-ray sensor, and separate as the multiple x-ray sources are positioned further away from the x-ray sensor, wherein positioning relative to the x-ray sensor is determined at least in part by the positioning sensor.

20. The three-dimensional radiographic imaging system of claim 15, further comprising:
a display configured to render the three-dimensional representation based on the set of converging angles.

* * * * *